United States Patent
Chen et al.

[19]

[11] Patent Number: 5,902,603
[45] Date of Patent: May 11, 1999

[54] POLYURETHANE HYDROGEL DRUG RESERVOIRS FOR USE IN TRANSDERMAL DRUG DELIVERY SYSTEMS, AND ASSOCIATED METHODS OF MANUFACTURE AND USE

[75] Inventors: Tung-Fen Chen, Sunnyvale; Chia-Ming Chiang, Foster City; Janan Jona, Sunnyvale; Priti Joshi, San Jose; Asha Ramdas, Mountain View, all of Calif.

[73] Assignee: Cygnus, Inc., Redwood City, Calif.

[21] Appl. No.: 08/713,711

[22] Filed: Sep. 13, 1996

Related U.S. Application Data

[63] Continuation-in-part of application No. 08/581,128, Dec. 29, 1995, abandoned, which is a continuation-in-part of application No. 08/528,105, Sep. 14, 1995, abandoned.

[51] Int. Cl.$^6$ .............. A61L 15/16; A61F 13/02
[52] U.S. Cl. .......... 424/449; 424/448; 424/486; 424/DIG. 7; 607/307; 514/772.3
[58] Field of Search .................. 424/435, 447, 424/448, 449, 486, DIG. 7; 604/307; 428/423.4; 514/772.3; 252/315.1

[56] References Cited

U.S. PATENT DOCUMENTS

| | | | |
|---|---|---|---|
| 4,220,152 | 9/1980 | Dresback | 128/260 |
| 4,379,454 | 4/1983 | Campbell et al. | 604/897 |
| 4,438,258 | 3/1984 | Graham | 528/361 |
| 4,644,033 | 2/1987 | Gnanou et al. | 524/590 |
| 4,698,062 | 10/1987 | Gale et al. | 604/896 |
| 4,849,224 | 7/1989 | Chang et al. | 424/434 |
| 4,914,173 | 4/1990 | Ansell | 528/49 |
| 5,000,955 | 3/1991 | Gould et al. | 424/409 |
| 5,160,328 | 11/1992 | Cartmell et al. | 604/307 |
| 5,352,508 | 10/1994 | Cheong | 428/264 |
| 5,423,737 | 6/1995 | Cartmell et al. | 602/57 |

FOREIGN PATENT DOCUMENTS

| | | |
|---|---|---|
| 0 528 091 A1 | 2/1993 | European Pat. Off. . |
| 91/05809 | 5/1991 | WIPO . |
| 92/20324 | 11/1992 | WIPO . |
| 97/09971 | 3/1997 | WIPO . |
| 97/24148 | 7/1997 | WIPO . |

*Primary Examiner*—Thurman K. Page
*Assistant Examiner*—Kathryne E. Shelborne
*Attorney, Agent, or Firm*—Barbara G. McClung; Angela Horne; Bozicevic & Reed LLP

[57] ABSTRACT

High capacity drug reservoirs are provided for incorporation into transdermal drug delivery systems. The drug reservoirs are hydrogels formulated from polyurethanes crosslinked with diisocyanate crosslinking agents or cured with radiation in the presence of a photoinitator. Drug loading as high as 65 to 70 wt. % or higher can be achieved by absorbing drug formulation into the reservoir after hydrogel synthesis. Methods for making and using transdermal systems containing such reservoirs are provided as well.

27 Claims, 5 Drawing Sheets

| FORMULATION # | PLATFORM |
|---|---|
| 1. | HYDROGEL (LAURIC ACID:ML:BD 20:40:40) |
| 2. | HYDROGEL (LAURYL ALCOHOL:ML:BD 20:40:40) |
| 3. | HYDROGEL (BENZYL ALCOHOL:ML:BD 20:40:40) |

FIG. 4

| FORMULATION # | PLATFORM |
|---|---|
| 1. | HYDROGEL (LAURIC ACID:ML:BD 20:40:40) |
| 2. | HYDROGEL (LAURYL ALCOHOL:ML:BD 20:40:40) |
| 3. | HYDROGEL (BENZYL ALCOHOL:ML:BD 20:40:40) |

FIG. 5

POLYURETHANE HYDROGEL DRUG RESERVOIRS FOR USE IN TRANSDERMAL DRUG DELIVERY SYSTEMS, AND ASSOCIATED METHODS OF MANUFACTURE AND USE

CROSS-REFERENCE TO RELATED APPLICATION

This is a continuation-in-part of U.S. patent application Ser. No. 08/581,128, filed Dec. 29, 1995, now abandoned which was a continuation-in-part of U.S. patent application Ser. No. 08/528,105, filed Sep. 14, 1995 now abandoned.

TECHNICAL FIELD

This invention relates generally to transdermal drug delivery, and more particularly relates to polyurethane hydrogel drug reservoirs for incorporation into transdermal drug delivery systems. The invention further relates to transdermal drug delivery systems containing the hydrogel reservoirs, and to methods for manufacturing and using the new transdermal systems.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most cases a substantially impermeable barrier to drug penetration.

Relatively recent advances in transdermal drug delivery have enabled effective administration of a variety of drugs through the skin. These advances include the development of a number of skin penetration enhancing agents, or "permeation enhancers," to increase the permeability of the skin or mucosal tissue, as well as non-chemical modes for facilitating transdermal delivery, e.g., the use of iontophoresis, electroporation or ultrasound. Nevertheless, the number of drugs that can be safely and effectively administered through the skin, without concomitant problems such as irritation or sensitization, remains limited.

The present invention is directed to transdermal drug delivery using "high capacity" hydrogel drug reservoirs into which a far greater quantity of drug may be present than possible with conventional transdermal systems. Thus, greater quantities of drug may be delivered, at higher fluxes.

In addition, the high capacity drug reservoirs, also reduce or in some cases eliminate the need for permeation enhancers. Further, smaller transdermal patches may be made using the inventive technology, i.e., patches that are at least as effective as prior patches in terms of overall drug release and drug flux, but are significantly reduced in terms of size.

While hydrogels have been described as potentially useful in drug delivery systems (see, e.g., P. I. Lee, *J. Controlled Release* 2:277–288 (1985)), their use in transdermal systems, and particularly the use of polyurethane hydrogels, is believed to be novel. None of the art of which applicants are aware describes transdermal drug delivery system having high capacity, polyurethane hydrogel drug reservoirs, nor does the art disclose methods for manufacturing such systems as disclosed and claimed herein.

The invention may be used to deliver a wide variety of drugs. For example, the present drug delivery systems may be used in the transdermal administration of 2-methyl-10-(4-methyl-1-piperazinyl)-4H-thieno[2,3-b][1,5] benzodiazepine, also known as "olanzapine." The drug is described in U.S. Pat. No. 5,229,382 to Chakrabarti et al., issued Jul. 20, 1993, and assigned to Lilly Industries Limited. Reference may be had thereto for any information concerning methods for synthesizing or using olanzapine not explicitly included herein.

Olanzapine is an antagonist of dopamine at the D-1 and D-2 receptors, and in addition has antimuscarinic anticholinergic properties and antagonist activity at 5HT-2 receptor sites and at noradrenergic α-receptors (Moore et al., *J. Pharmacol. Exp. Ther.* 262(2):545–551 (1992)). The drug has relaxant, anxiolytic and anti-emetic properties, and, as explained in the Chakrabarti et al. patent, is useful in the treatment of psychosis, acute mania and mild anxiety states, and is particularly useful in the treatment of schizophrenia and schizophreniform illnesses.

Currently, olanzapine is administered orally or by injection. While the drug has been established as an effective antipsychotic agent, drug non-compliance is a serious problem, and is believed to account for approximately one-third of all short-stay hospital costs. Transdermal administration of olanzapine or a pharmaceutically acceptable salt thereof, significantly enhances patient compliance by providing an advanced delivery system useful for administering the drug over an approximately three- to seven-day period. There are a number of other advantages to administering olanzapine transdermally as well: gastrointestinal and other side effects associated with oral administration are substantially avoided; continuous delivery provides for sustained blood levels; the transdermal patch is easily removable if any side effects do occur; and the likelihood of patient acceptance is significantly improved. In general, steady-state, transdermal delivery of the drug seems to provide a far better side effect profile overall than is associated with oral administration.

The present systems are also useful in the transdermal administration of steroid drugs, including androgenic agents. Particular compounds of interest are testosterone and pharmaceutically acceptable esters and derivatives thereof. Such agents are useful in a variety of applications, e.g., in treating hypogonadism, hypopituitarism, Addison's disease, impotence, male infertility disorders, anemia, and in male hormone replacement therapy. The invention also involves the transdermal administration of androgenic agents in combination with estrogens, in treating, for example, menopause, osteoporosis, or other conditions for which estrogen-androgen combination therapy is indicated.

Transdermal delivery of androgens, alone or in combination with estrogenic agents, has been described. See, e.g., U.S. Pat. No. 4,704,282 to Campbell et al., U.S. Pat. No. 4,867,982 to Campbell et al., U.S. Pat. No. 5,094,857 to Luderschmidt, U.S. Pat. No. 5,152,997 to Ebert et al., U.S. Pat. No. 5,460,820 to Ebert et al., and PCT Publication No. WO95/03764. In contrast to prior systems for administering these drugs transdermally, however, the present invention is directed transdermal systems in which the androgenic agent is contained within drug reservoirs into which a far greater quantity of drug may be loaded than possible with conventional transdermal systems. As explained above, such systems provide a number of advantages, including delivery of greater quantities of drug, at higher fluxes, reduction of patch size, and the like.

The following references are of interest insofar as they pertain to the subject matter of the invention:

U.S. Pat. No. 4,438,258 to Graham describes a wound dressing of a hydrogel comprised of a polymerizable cyclic thioether and at least one hydrophilic homo- or copolymer, which may contain a urethane functionality.

U.S. Pat. No. 4,644,033 to Gnanou et al. relates to contact lenses of polyurethane hydrogels formed by crosslinking polyoxyethylene with a polyfunctional isocyanate.

U.S. Pat. No. 5,160,328 to Cartmell et al. describes a self-adhesive bandage having a polyurethane hydrogel layer stated to be suitable for absorbing bodily fluids. The hydrogel is formed from a polyhydric alcohol, an isophoronediisocyanate-terminated prepolymer, a polyethylene oxide based diamine, sodium chloride and water.

U.S. Pat. No. 5,352,508 to Cheong relates to wound dressings comprising a polyurethane matrix formed by reacting a polyisocyanate with an excess of a polyhydroxy compound.

SUMMARY OF THE INVENTION

Accordingly, it is a primary object of the present invention to provide a high capacity, polyurethane hydrogel drug reservoir for transdermal administration of a drug formulation contained therein.

It is another object of the invention to provide a transdermal drug delivery system containing a high capacity, polyurethane hydrogel drug reservoir.

It is still another object of the invention to provide a method for making such a drug delivery system.

It is a further object of the invention to provide a method for administering a drug to an individual using the novel reservoirs and transdermal drug delivery systems containing them.

Additional objects, advantages and novel features of the invention will be set forth in part in the description which follows, and in part will become apparent to those skilled in the art upon examination of the following, or may be learned by practice of the invention.

The present invention is thus directed in part to high capacity, polyurethane hydrogel reservoirs useful in transdermal drug delivery systems, which, by virtue of the novel reservoirs, are able to deliver greater quantities of drug, at higher fluxes, than possible with conventional transdermal systems. The hydrogel reservoirs may also reduce or in some cases eliminate the need for permeation enhancers. For those drugs which do still require the presence of an enhancer to achieve high flux, the hydrogel reservoirs provide a means whereby augmented loading of both drug and enhancer may be achieved.

Transdermal drug delivery systems containing the novel reservoir will generally comprise a laminated composite of at least: (a) a backing layer that is substantially impermeable to the drug and defines the upper surface of the system during drug delivery; and (b) the high capacity reservoir in the form of a polyurethane hydrogel having a predetermined quantity of a drug formulation contained therein. The hydrogel may have sufficient tack to enable the transdermal system to adhere to the skin or mucosal tissue; however, in some cases, it may be necessary to incorporate an added means for affixing the composite to the body surface, typically either an "in-line" contact adhesive in the form of a layer underlying the entire surface of the system, or a peripheral adhesive ring.

Additional materials and components may also be present. For example, in some cases, it may be preferable or necessary to incorporate a rate-controlling membrane into the transdermal system. One or more additional reservoir and/or adhesive layers may also be included. Also, during storage and prior to use, a release liner should be present to protect the basal surface of the system.

The invention is also directed to a method for preparing a transdermal drug delivery system having a high capacity, polyurethane hydrogel drug reservoir, comprising: (a) reacting a polyurethane with a crosslinking agent in the presence of water, for a time period effective to form a hydrogel; (b) absorbing a drug formulation into the hydrogel to form a drug-containing hydrogel; and (c) laminating a backing layer to the hydrogel that is substantially impermeable to the drug and serves as the upper surface of the system during drug delivery. Steps (a) and (b) may be conducted simultaneously, although it is preferred, to achieve higher drug loading, that step (b) follow step (a).

The invention further provides a method for transdermally administering a drug to a mammalian individual, comprising positioning topically on the individual a transdermal drug delivery system containing a high capacity drug reservoir of a polyurethane hydrogel as provided herein.

The systems are useful, for example, in the transdermal administration of androgenic agents such as testosterone. Administration is conducted for a time period and at an administration rate effective to provide the necessary therapy, e.g., treatment of impotence, infertility disorders, or the like. Using high capacity, polyurethane hydrogel reservoirs, transdermal patches on the order of 30 cm$^2$ or smaller may be used to deliver the selected androgenic agent, while still achieving a drug flux that is for all contemplated indications more than sufficient. Optimally, the androgenic agent patches are designed to be worn for 24-hour periods.

The systems are also useful in transdermally administering olanzapine or a pharmaceutically acceptable salt thereof, to treat an individual suffering from or susceptible to psychosis, acute mania or mild anxiety states, particularly schizophrenia and schizophreniform illnesses. Transdermal administration of olanzapine is conducted for a time period and at an administration rate effective to alleviate the symptoms at issue. The preferred transdermal system used for administration of olanzapine or a pharmaceutically acceptable salt thereof is as described above, i.e., it will typically be a laminated composite comprised of a backing layer, the high capacity, polyurethane hydrogel reservoir, a means for affixing the composite to the selected area of body surface, and, optionally, other membranes and components as well. The transdermal system is preferably constructed such that an effective dose of olanzapine or a pharmaceutically acceptable acid addition salt thereof will be delivered for a period in the range of about three to seven days.

DETAILED DESCRIPTION OF THE INVENTION

Before describing the present invention in detail, it is to be understood that this invention is not limited to particular transdermal drug delivery system configurations, particular drug/vehicle formulations, or the like, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a permeation enhancer" includes a mixture of two or more permeation enhancers, reference to "an excipient" or "a vehicle" includes mixtures of excipients or vehicles, reference to "an adhesive layer" includes reference to two or more such layers, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

By "transdermal" delivery, applicants intend to include both transdermal (or "percutaneous") and transmucosal administration, i.e., delivery by passage of a drug through the skin or mucosal tissue and into the bloodstream. The term "body surface" will sometimes be used herein to refer to either the skin or the mucosal tissue.

By a "high capacity" drug reservoir, as used herein, is meant a drug reservoir containing a quantity of drug or drug formulation which is greater than that which is typically possible using conventional manufacturing techniques or transdermal drug delivery systems; the drug reservoirs herein can be made so as to contain on the order of 65 wt. % to 70 wt. % drug formulation or more.

The term "hydrogel" is used in its conventional sense to refer to a water-swellable polymeric matrix in which a dispersed, polymeric phase has combined with a continuous, aqueous phase to form a viscous, colloidal product.

The term "urethane" is used herein in its conventional sense to denote organic compounds containing a recurring —O—(CO)—NH— linkage. The term "polyurethane" is intended to mean a polymer, either a homopolymer or copolymer, containing a plurality of urethane units as just defined.

By an "effective" amount of a drug is meant a nontoxic but sufficient amount of the drug to provide the desired therapeutic or prophylactic effect. With respect to olanzapine, for example, an "effective" amount of drug refers to that dose of drug which will be effective in relieving or preventing symptoms of psychosis, acute mania, mild anxiety, or the like. An "effective" amount of a permeation enhancer as used herein means an amount that will provide the desired increase in the permeability of the skin or mucosal tissue, and, correspondingly, the desired depth of penetration, rate of administration, and amount of drug delivered.

By "predetermined area of skin" is intended a defined area of intact unbroken living skin or mucosal tissue. That area will usually be in the range of about 5 cm$^2$ to about 150 cm$^2$, more usually in the range of about 5 cm$^2$ to about 100 cm$^2$, and preferably in the range of about 5 cm$^2$ to about 60 cm$^2$. However, it will be appreciated by those skilled in the art of transdermal drug delivery that the area of skin or mucosal tissue through which drug is administered may vary significantly, depending on patch configuration, dose, and the like. Also, above, the present technology enables preparation of generally smaller patches, typically in the range of about 5 cm$^2$ to about 50 cm$^2$.

"Penetration enhancement" or "permeation enhancement" as used herein relates to an increase in the permeability of skin or mucosal tissue to a pharmacologically active agent, i.e., so as to increase the rate at which the drug permeates through the body surface and enters the bloodstream. The enhanced permeation effected through the use of such enhancers can be observed by measuring the rate of diffusion of drug through animal or human skin using a diffusion cell apparatus as described in the Examples herein.

"Carriers" or "vehicles" as used herein refer to carrier materials suitable for transdermal drug administration, and include any such materials known in the art, e.g., any liquid, gel, solvent, liquid diluent, solubilizer, or the like, which is nontoxic and which does not interact with other components of the composition in a deleterious manner. Examples of suitable carriers for use herein include water, silicone, liquid sugars, waxes, petroleum jelly, and a variety of other materials. The term "carrier" or "vehicle" as used herein may also refer to stabilizers, crystallization inhibitors, or other types of additives useful for facilitating transdermal drug delivery.

By the term "saturated," as used in conjunction with the transdermal delivery of androgenic agents, is meant a pharmaceutical formulation in which the drug is present at saturation; when the present systems are used for the administration of an androgenic agent, the drug is present in the pharmaceutical formulation contained in the drug reservoir at or above saturation.

When transdermal administration of "olanzapine" per se is indicated herein, it is to be understood that the described method, formulation or system extends to pharmaceutically acceptable acid addition salts as well.

The drug reservoirs of the present transdermal drug delivery systems are polyurethane hydrogel matrices. Generally, these matrices are formed by admixing a polyurethane with a suitable crosslinking agent in the presence of water. Drug formulation may be incorporated during hydrogel manufacture, i.e., admixed with the polyurethane along with the crosslinking agent and water, or it may be incorporated into the hydrogel matrix after addition of water.

Suitable polyurethanes useful for forming the hydrogel reservoir may be chemically synthesized using conventional techniques known to those skilled in the art or described in the pertinent literature. The polyurethanes can be polyurethane elastomers such as those available as Airthane®, Polathane®, Ultracast® and Cyanaprene® from Air Products and Chemicals Inc., as Conathane® from Conap, Inc., as Bayte C®, Baymidur Vul Kollan®, Baydur®, Bayflex® or Baygal® from Miles Inc., Polymers, Division; alternatively, polyurethane resins such as Desmodur® or Mondur® resins, which can be obtained from Miles, Inc., Industrial Chemicals Division, can be used. Hydrophilic polyurethane prepolymers such as those available under the Hypol® trademark from W. R. Grace & Co., Organic Chemicals Division, may be used as well, and are particularly preferred; and an example of a particularly effective commercially available polyurethane that can be used in conjunction with the present invention is Hypol® PreMA G-50 polymer, available from the Hampshire Chemical Corporation.

In order to form the hydrogel, as explained above, a crosslinking agent is added to the polyurethane in the presence of water. Preferred crosslinking agents are diisocyanates, including aliphatic, cycloaliphatic and aromatic diisocyanates. Suitable diisocyanates include, but are not limited to, tetramethylene diisocyanate, hexamethylene diisocyanate, trimethylene diisocyanate, trimethylhexamethylene diisocyanate, cyclohexyl-1,2-diisocyanate, cyclohexylene-1,4-diisocyanate, 2,4-toluene diisocyanate, and 2,6-toluene diisocyanate. The amount of crosslinking agent used will be such that it is effective to produce the desired hydrogel, but preferably less than that which would result in any unconsumed material. However, if excess crosslinking agent is present after hydrogel formation, it may be removed using a simple washing step.

Generally, the reaction mixture for forming the polyurethane hydrogel will contain about 5 wt. % to 25 wt. % isocyanate crosslinking agent and about 0.01 wt. % to 15 wt. % water, with the polyurethane representing the remainder of the composition, along with the drug formulation, if it is incorporated during manufacture. It will be appreciated by those skilled in the art, however, that the various components of the reservoir may need to be varied, e.g., depending on the degree of tack desired (which would in turn necessitate a higher fraction of water) or on some other desired characteristic of the final product.

The drug formulation may be incorporated into the hydrogel during hydrogel formation or subsequent thereto. Generally, the latter procedure is preferred, as a greater degree of drug may be incorporated into the hydrogel; that is, by absorbing drug into the hydrogel after the hydrogel is prepared, drug loading of at least about 40 wt. %, and preferably on the order of 65 wt. % to 70 wt. % or higher can be achieved.

In an alternative embodiment, a photocurable polyurethane is used at the outset, to form the hydrogel. In such a case, curing may be effected using radiation of a suitable wavelength, rather than a crosslinking agent. Photocuring can in some cases be neater, and done more rapidly, than curing using a diisocyanate-type crosslinking agent. With photocuring, it is typically necessary to carry out the curing step in the presence of a photoinitiator. Suitable photoinitiators are radical photoinitiators that are well known to those skilled in the art. Examples of such photoinitiators include α-alkoxy deoxybenzoins, α,α-dialkoxy deoxybenzoins, α,α-dialkoxy acetophenones, 2-hydroxy-2, 2-dialkyl acetophenones, benzophenones, thioxanthones, benzils, and other compounds identified by H. J. Hageman et al., "Photoinitiators and Photocatalysts for Various Polymerisation and Crosslinking Processes," in *Radiation Curing of Polymers II*, ed. D. R. Randell (The Royal Society of Chemistry, 1991), at pp. 46–53.

The reservoir layer will generally although not necessarily range in thickness from about 1 to about 100 mils, preferably in the range of approximately 25 to 60 mils. It will be appreciated that the thickness of the reservoir will depend, however, on a variety of considerations, including the quantity of drug to be incorporated in the reservoir, desired patch size, and the like.

After fabrication of the hydrogel reservoir and incorporation of drug therein, the remainder of the transdermal system is manufactured. It will be appreciated by those skilled in the art that any number of patch configurations may be used in conjunction with the present drug reservoirs; the following structures are described by way of example only, and are not intending to be limiting.

Generally, although not necessarily, a backing layer is laminated to the hydrogel reservoir following reservoir preparation. The backing layer functions as the primary structural element of the system and provides the system with much of its flexibility, drape and, preferably, occlusivity. The material used for the backing layer should be inert and incapable of absorbing drug, enhancer or other components of the pharmaceutical composition contained within the system. The backing is preferably made of one or more sheets or films of a flexible elastomeric material that serves as a protective covering to prevent loss of drug and/or vehicle via transmission through the upper surface of the system, and will preferably impart a degree of occlusivity to the system, such that the area of the skin covered on application becomes hydrated. The material used for the backing layer should permit the system to follow the contours of the skin and be worn comfortably on areas of skin such as at joints or other points of flexure, that are normally subjected to mechanical strain with little or no likelihood of the system disengaging from the skin due to differences in the flexibility or resiliency of the skin and the system. Examples of materials useful for the backing layer are polyesters, polyethylene, polypropylene, polyurethanes and polyether amides. The layer is preferably in the range of about 15 microns to about 250 microns in thickness, and may, if desired, be pigmented, metallized, or provided with a matte finish suitable for writing.

Underneath the hydrogel reservoir, i.e., on the "skin" side thereof, may be a pharmaceutically acceptable contact adhesive for affixing the system to the skin during drug delivery. With hydrogels which adhere well to the skin or mucosal tissue, use of a contact adhesive is unnecessary. Most hydrogels, however, will not adhere sufficiently, and a contact adhesive or some other means for maintaining the system in drug transmitting relationship to the skin is required. If a contact adhesive is used, it may be in the form of a layer which covers the entire drug reservoir, thus serving as the basal surface of the system during use, or it may be in the form of a peripheral ring. Suitable contact adhesive materials are pressure-sensitive adhesives suitable for long-term skin contact, which are also be physically and chemically compatible with the drug formulation, i.e., the drug itself and any carriers and vehicles employed. It is essential that the contact adhesive not comprise a drug-absorbent material, as such a material would inhibit drug flux. Preferred materials for this layer include, for example, polysiloxanes, polyisobutylenes, polyacrylates, polyurethanes, plasticized ethylene-vinyl acetate copolymers, low molecular weight polyether amide block polymers (e.g., PEBAX), tacky rubbers such as polyisobutene, polystyrene-isoprene copolymers, polystyrene-butadiene copolymers, and mixtures thereof.

It may also be desirable to include a rate-controlling membrane in between the drug reservoir and a contact adhesive layer, when one is present. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, and the like. Generally, a preferred material useful to form the rate-controlling membrane is ethylene-vinyl acetate copolymer. The particular material selected will be such that the flux of drug component or of one or more non-drug components, i.e., will be controlled as desired.

Additionally, to protect the basal surface of the system during storage and just prior to use, a release liner is provided to cover the exposed hydrogel or adhesive surface. The release liner is a disposable element, typically formed from a material impermeable to the drug, vehicle and adhesive, and which is easily stripped from the contact adhesive. Release liners are typically treated with silicone or fluorocarbons. Silicone-coated polyester is presently preferred.

Figure 1:
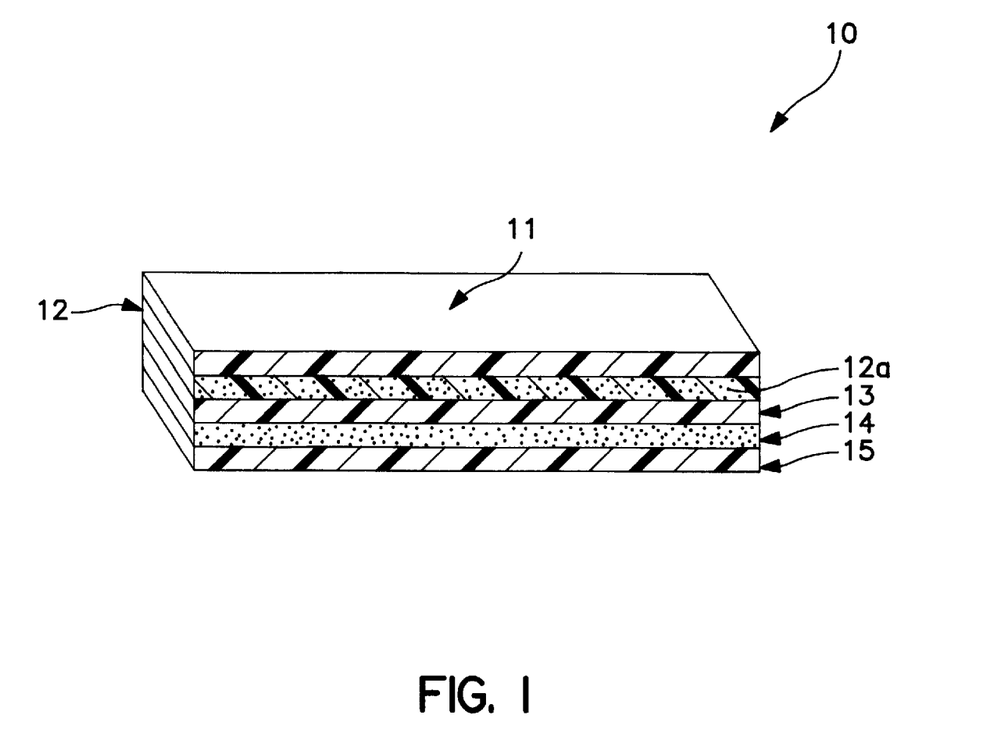
FIG. 1 illustrates in schematic form one embodiment of a transdermal drug delivery system which can be used in conjunction with the manufacturing methodology and hydrogel reservoirs of the invention.

An example of a laminated composite containing a hydrogel reservoir of the invention is shown in FIG. 1. The composite is generally designated 10, and comprises a backing layer 11, the hydrogel reservoir layer 12 containing drug 12a, optional rate-controlling membrane 13, optional contact adhesive layer 14, and a release liner 15. As noted above, adhesive may also be present as a peripheral ring on the basal surface of the system.

Any number of drugs may be delivered transdermally using the reservoirs and drug delivery systems of the invention, i.e., any compound suitable for transdermal or transmucosal administration which induces a desired systemic effect. Such substances include the broad classes of compounds normally delivered through body surfaces and membranes, including skin. In general, this includes: anti-infectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmic; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers. The amount of active agent incorporated into the drug reservoir will vary, depending on the agent, the intended dosage, the individual undergoing treatment, the particular indication, and the like.

It is important to note that the present invention enables transdermal delivery of drugs which typically display low skin flux, as the quantity of drug which may be loaded into the high capacity drug reservoir is significantly greater than with conventional systems. Other preferred drugs are those that require high flux to achieve a desired therapeutic effect and thus may require the presence of an enhancer in the drug formulation. The present invention provides a drug reservoir comprising a polyurethane hydrogel that, for the same size patch, is capable of absorbing not only more drug than prior patches but is also capable of absorbing more enhancer as well.

Steroids represent one class of drugs with which the present reservoirs and transdermal systems are particularly useful. Examples of steroid drugs which may be administered in conjunction with the invention include: progestogens such as flurogestone acetate, hydroxyprogesterone, hydroxyprogesterone acetate, hydroxyprogesterone caproate, medroxyprogesterone acetate, norethindrone, norethindrone acetate, norethisterone, norethynodrel, desogestrel, 3-keto desogestrel, gestadene and levonorgestrel; estrogens such as estradiol and its esters (e.g., estradiol benzoate, valerate, cypionate, decanoate and acetate), ethynyl estradiol, estriol, estrone and mestranol; and corticosteroids such as betamethasone, betamethasone acetate, cortisone, hydrocortisone, hydrocortisone acetate, corticosterone, fluocinolone acetonide, prednisolone, prednisone and triamcinolone.

Also, in one specific embodiment of the invention, the present transdermal systems are used to administer androgenic agents such as the naturally occurring androgens androsterone and testosterone; pharmaceutically acceptable esters of testosterone, typically esters formed from the hydroxyl group present at C-17, and particularly the enanthate, propionate, cypionate and phenylacetate esters; and pharmaceutically acceptable derivatives of testosterone such as methyltestosterone, testolactone, oxymetholone and fluoxymesterone. Testosterone and the 17-esters thereof, particularly the enanthate, propionate and cypionate esters, are preferred. Such agents are useful in a variety of applications, e.g., in male hormone therapy, in treating hypogonadism, hypopituitarism, Addison's disease, impotence, male infertility disorders, anemia, and the like. Other pharmaceutically active agents, particularly additional steroidal agents, may be administered along with the selected androgenic agent. These agents will generally be estrogens and/or progestogens. The amount of each such additional agent incorporated into the drug reservoir will vary, depending on the intended dosage. Normally, the daily dosage of estrogenic agent will be at least about 0.03 mg/day, while the daily dosage of progestogen will be at least about 0.2 mg/day, depending, of course, on the particular estrogen and progestogen to be administered. Administration of an androgenic agent in combination with an estrogen and/or a progestogen is useful, for example, in the treatment of menopausal symptoms, osteoporosis, or other conditions for which such combination therapy is indicated.

When the present invention is used in conjunction with the delivery of androgenic agents, administration is conducted for a time period and at an administration rate effective to provide the necessary therapy, e.g., treatment of impotence, infertility disorders, or the like. The agent should be delivered at a dosage of at least about 3 mg/day, more preferably at least about 6 mg/day. Transdermal patches on the order of 30 cm$^2$ or smaller may be used to deliver the selected androgenic agent, while still achieving a drug flux that is for all contemplated indications more than sufficient. Generally, a flux of at least about 100, more preferably at least about 200 μg/cm$^2$/day, is necessary. The present drug reservoirs achieve such fluxes. Optimally, the androgenic agent patches are designed to be worn for 24-hour periods.

While not essential, it is preferred that transdermal administration of androgenic agents be conducted at or above saturation. That is, the androgenic agent is present at or above saturation with respect to its concentration in the formulation contained in the drug reservoir.

The reservoirs and transdermal systems of the invention are also useful in the transdermal administration of olanzapine. The specific method and drug delivery system for delivering olanzapine transdermally may vary, but necessarily involve application of a drug delivery system containing olanzapine or a pharmaceutically acceptable acid addition salt thereof to a predetermined area of the skin or mucosal tissue at an administration rate and for a period of time sufficient to provide an effective blood level of drug for a desired period of time. The drug is present in a high capacity, superabsorbent drug reservoir within a transdermal delivery system such as the exemplary system described above. It should be noted that this embodiment of the invention, while primarily directed to the treatment of individuals suffering from or susceptible to psychosis, acute mania or mild anxiety states, may extend to any use of olanzapine deriving from its activity an antagonist of dopamine at the D-1 and D-2 receptors, its antimuscarinic anti-cholinergic properties, and/or its antagonist activity at 5HT-2 receptor sites and noradrenergic α-receptors. The transdermal olanzapine system formulated using the novel reservoirs are preferably constructed so that an effective dose of olanzapine or a pharmaceutically acceptable salt thereof will be delivered for a period in the range of about three to seven days.

Olanzapine or any other basic drug may be administered in the form of the base or as a pharmaceutically acceptable acid addition salt. As will be appreciated by those skilled in the art, the base form of the drug can be converted to an acid addition salt by treatment with a stoichiometric excess of a selected acid. Such acid addition salts may be formed, for example, with inorganic acids such as hydrochloric acid, hydrobromic acid, sulfuric acid, nitric acid, phosphoric acid, and the like, or with organic acids such as acetic acid, propionic acid, glycolic acid, pyruvic acid, oxalic acid, malic acid, malonic acid, succinic acid, maleic acid, hydroxymaleic acid, fumaric acid, tartaric acid, citric acid, benzoic acid, cinnamic acid, mandelic acid, methanesulfonic acid, ethanesulfonic acid, p-toluenesulfonic acid, naphthalene-2-sulfonic acid, salicylic acid and the like.

Similarly, acidic drugs may be administered in the acid form or, as will be appreciated by those skilled in the art, as a pharmaceutically basic salt. The salts may be derived from inorganic bases, e.g., the ammonium, potassium, sodium, calcium and magnesium salts. Alternatively, the salts may be derived from pharmaceutically acceptable nontoxic bases, including isopropylamine, trimethylamine, dimethylamine, triethylamine, ethanolamine, dicyclohexylamine, choline, tromethylamine, and the like.

The high capacity hydrogel reservoirs of the invention may in some cases eliminate the need for a permeation enhancer. However, enhancers may still be preferred or even required for administering certain drugs, e.g., steroids, including androgenic agents, and olanzapine. Suitable enhancers include, but are not limited to, dimethylsulfoxide (DMSO), dimethyl formamide (DMF), N,N-dimethylacetamide (DMA), decylmethylsulfoxide (C$_{10}$MSO), polyethylene glycol monolaurate (PEGML), propylene glycol (PG), propylene glycol monolaurate (PGML), glycerol monolaurate (GML), methyl laurate (ML), lauryl lactate (LL), isopropyl myristate (IPM), terpenes such as menthone, C$_2$–C$_6$ diols, particularly 1,2-butanediol and 1,3-butanediol (1,2-BD and 1,3-BD), lecithin, the 1-substituted azacycloheptan-2-ones, particularly 1-n-dodecylcyclazacycloheptan-2-one (available under the trademark Azone® from Whitby Research Incorporated, Richmond, Va.), alcohols, and the like. Vegetable oil permeation enhancers, as described in commonly assigned U.S. Pat. No. 5,229,130 to Sharma, may also be used. Such oils include, for example, safflower oil, cotton seed oil and corn oil.

Preferred enhancers for use in conjunction with the present invention, and particularly in the transdermal administration of androgenic agents and olanzapine, are esters given by the formula [CH$_3$(CH$_2$)$_m$COO]$_n$R in which m is an integer in the range of 8 to 16, n is 1 or 2, and R is a lower alkyl (C$_1$–C$_3$) residue that is either unsubstituted or substituted with one or two hydroxyl groups. In the preferred embodiment herein, the ester component is a lower alkyl (C$_1$–C$_3$) laurate (i.e., m is 10 and n is 1), and in a particularly preferred case is "PGML." It will be appreciated by those skilled in the art that the commercially available material sold as "PGML" is typically a mixture of propylene glycol monolaurate itself, propylene glycol dilaurate, and either propylene glycol, methyl laurate, or both. Thus, the terms "PGML" or "propylene glycol monolaurate" as used herein are intended to encompass both the pure compound as well as the mixture that is typically obtained commercially.

Also preferred are fatty acids and fatty alcohols corresponding to the above-defined fatty esters. Thus, fatty acids useful as permeation enhancers herein will generally have the formula CH$_3$(CH$_2$)$_m$COOH, where m is as above, while the fatty alcohols will have the formula CH$_3$(CH$_2$)$_m$CH$_2$OH.

Other preferred enhancer compositions are wherein a fatty ester as described above is combined with an ether component selected from the group consisting of diethylene glycol monoethyl ether and diethylene glycol monomethylether. Such enhancer compositions are described in detail in U.S. Pat. Nos. 5,053,227 and 5,059,426 to Chiang et al., both of common assignment herewith.

Particularly preferred permeation enhancers are selected from the group consisting of C$_2$–C$_6$ alkanediols, fatty esters having the structural formula [CH$_3$(CH$_2$)$_m$COO]$_n$R, fatty acids having the structural formula CH$_3$(CH$_2$)$_m$COOH, fatty alcohols having the structural formula CH$_3$(CH$_2$)$_m$CH$_2$OH, and mixtures thereof, where m and n are as defined above. It has been found that ternary vehicle combinations in which such a fatty alcohol or acid is combined with a fatty ester and a C$_2$–C$_6$ alkanediol, e.g., 1,2-butanediol, 1,3-butanediol, and the like, are particularly effective enhancer compositions for use in conjunction with the present invention.

If an enhancer is used, the type and amount of enhancer will similarly depend on a number of factors, e.g., the strength of the particular enhancer, the desired increase in skin permeability, rate of administration, and amount of drug delivered.

The drug formulations contained in the high capacity reservoirs may also include standard carriers or vehicles useful for facilitating drug delivery, e.g., stabilizers, antioxidants, anti-irritants and crystallization inhibitors.

Preferred drug formulations, i.e., the drug-containing composition which is loaded into the drug reservoir, will typically contain on the order of about 0.1 wt. % to 20 wt. %, preferably about 1 wt. % to 10 wt. % drug, with the remainder of the formulation representing other components such as enhancers, vehicles or the like. If enhancers are present, they will generally represent on the order of approximately 1 wt. % to 25 wt. % of the drug formulation.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

All patents, patent applications, and publications mentioned herein, both supra and infra, are hereby incorporated by reference.

Experimental

Materials: Olanzapine free base was provided by Eli Lilly. Testosterone was purchased from Sigma Chemical Company and used as received. All chemicals used were of reagent grade.

Preparation of Transdermal Systems: Drug was dissolved in selected vehicle combinations as indicated in the Examples below. Hydrogels were prepared as indicated in the individual examples, and cut into disks which were then applied to the skin.

Assay methodology: For evaluation of skin flux, samples were analyzed by HPLC using UV-detection at 265 nm and 220 nm. Chromatographic resolution was achieved using a Brownlee RP-18 column, 100 mm×4.6 mm, with a 5 $\mu$m particle size (for olanzapine), and a Zobrax $C_8$ column, 250 mm×4.6 mm, also with a 5 $\mu$m particle size (for testosterone), run at a flow rate of 1.5 ml per min (olanzapine) or 1.0 ml per minute (testosterone) at ambient temperature. The mobile phase was a mixture of 47%–48% acetonitrile: 52%–53% water. The retention time for olanzapine was about 3.0 min; the retention time for testosterone was about 4.0 min.

In Vitro Skin Permeation of Drug

Skin Preparation: Human cadaver skin was used for the permeation studies. The frozen skins were thawed and the epidermal layers (stratum corneum and viable epidermis) were separated from the full-thickness skin by immersing it in water at 60° C. for two min. This epidermis was either used immediately for flux studies or stored at −20° C. for later studies.

Skin permeation from prototypes: Modified Franz cells were used for evaluating the prototype systems for delivery of drug. Prototype systems, prepared as described above, were placed on top of the epidermis. Gentle pressure was applied to ensure full contact between the prototype and the stratum corneum. The skin membrane with the prototype system was then mounted carefully between the donor and the receiver compartments. The receiver compartment was filled with 7.5 ml of pH 7.4 buffer and the temperature was maintained at 32° C.+1° C. throughout the experimental period. The entire receiver content was withdrawn and replaced with fresh buffer. Samples were assayed by HPLC.

Data Analysis: Skin flux ($\mu$g/cm$^2$/hr) was determined at each time point by dividing the amount of drug penetrating the skin during that period of time corrected for the surface area by the duration of time.

EXAMPLE 1

Figure 2:
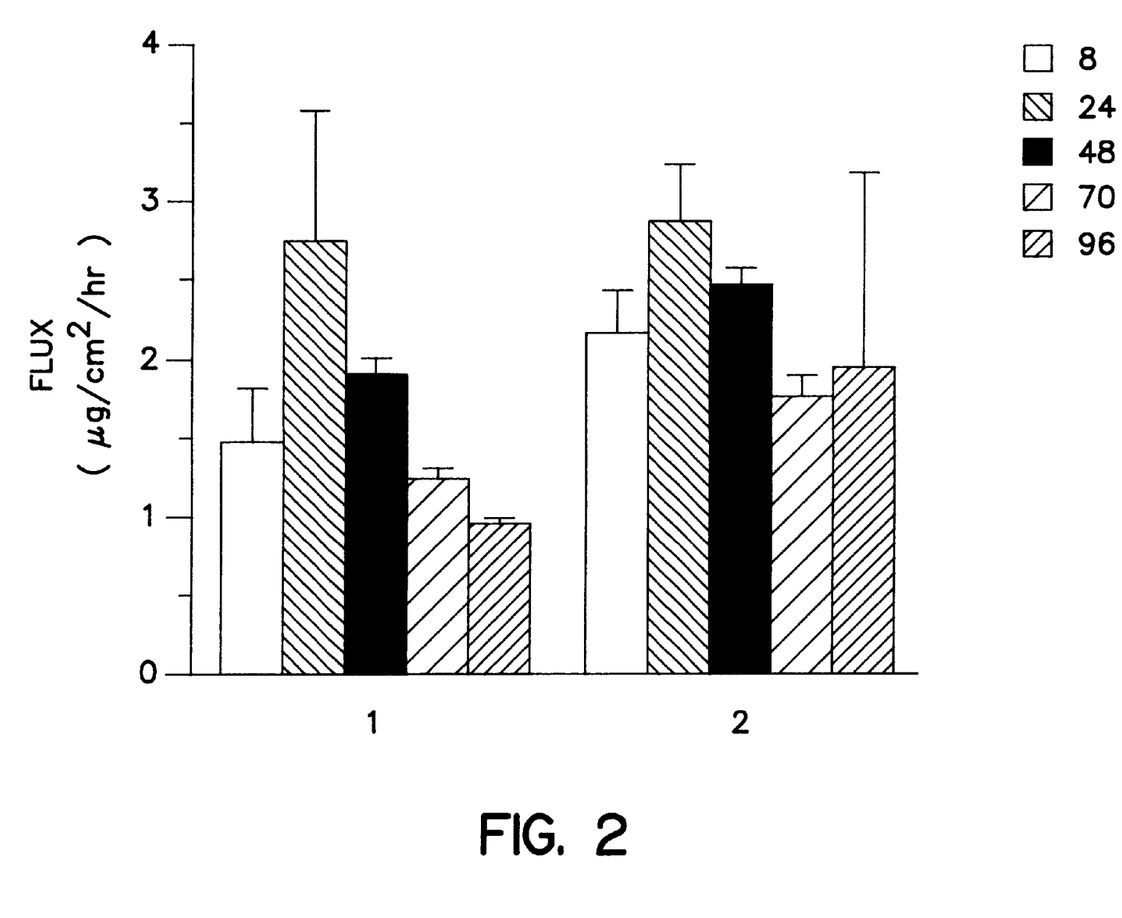
FIGS. 2 and 3 are graphs illustrating olanzapine flux obtained using the hydrogel systems prepared in Examples 1 and 2, respectively.

Olanzapine was dissolved in a combination of vehicles (see Table 1), added with water to Hypol® PreMA G-50 polymer (Hampshire Chemical Corporation) (the ratio of water to polymer was approximately 2:1) and mixed together until a hydrogel was formed. The gel was cut into 2 cm$^2$ area circles and applied onto human cadaver skin using a Franz diffusion cell. At predetermined times, the receiver fluid was replaced with fresh fluid and analyzed for olanzapine using HPLC. The formulations evaluated are listed in Table 1 and the skin flux results are shown in FIG. 2.

TABLE 1

| Formulation | |
|---|---|
| 1. | Hydrogel G-50 contains 25% Solution of saturated olanzapine in (10% Methyl Laurate + 45% Lauryl lactate + 45% 1,2-butanediol) |
| 2. | Hydrogel G-50 contains 25% Solution of saturated olanzapine in (10% Lauric acid + 45% Lauryl lactate + 45% 1,2-butanediol) |

EXAMPLE 2

Figure 3:
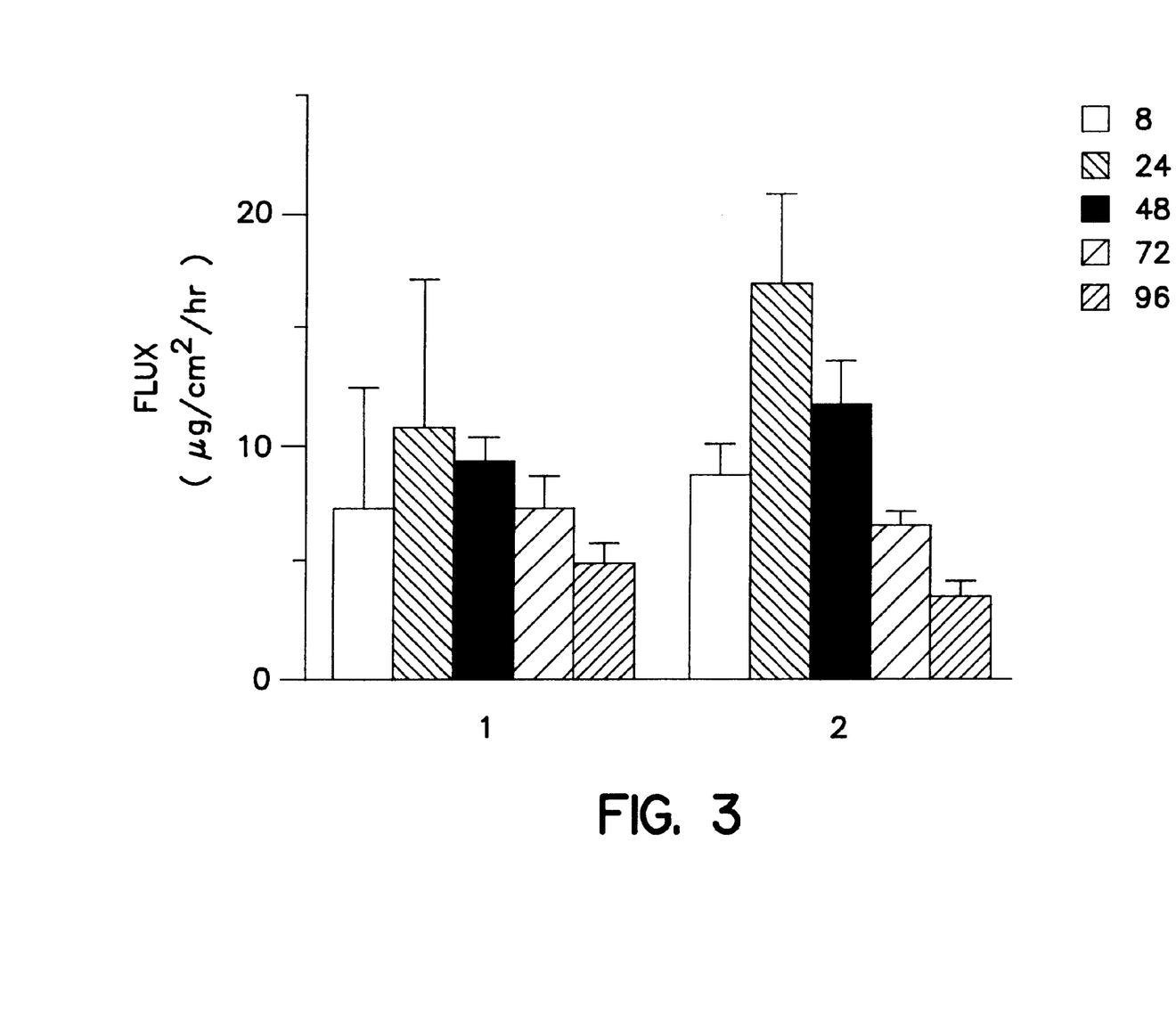

Olanzapine was dissolved in a combination of vehicles (as indicated in Table 2). Water was added to Hypol® PreMA G-50 polymer, as above (the ratio of water to polymer used was again approximately 2:1) and the solution mixed until a hydrogel was formed. The gel was cut into 2 cm$^2$ circles which were then soaked with drug formulations overnight. The final product was applied onto human cadaver skin, as in Example 1. The formulations are listed in Table 2 and the results are shown in FIG. 3.

TABLE 2

| Formulation | |
|---|---|
| 1. | Olanzapine saturated in 10% Lauric acid + 45% methyl Laurate + 45% 1,2-butanediol and left overnight with Hypol PreMA gel. |
| 2. | Olanzapine saturated in 10% Oleic acid + 45% methyl Caprate + 45% 1,2-butanediol and left overnight with Hypol PreMA gel. |

EXAMPLE 3

A skin flux study was conducted to evaluate the flux of testosterone from polyurethane hydrogel systems. Testosterone was dissolved in a combination of vehicles (see Table 3), added with water to Hypol® PreMA G-50 polymer, as in the preceding examples (the ratio of water to polymer was again approximately 2:1) and mixed together until a hydrogel was formed.

Figure 4:
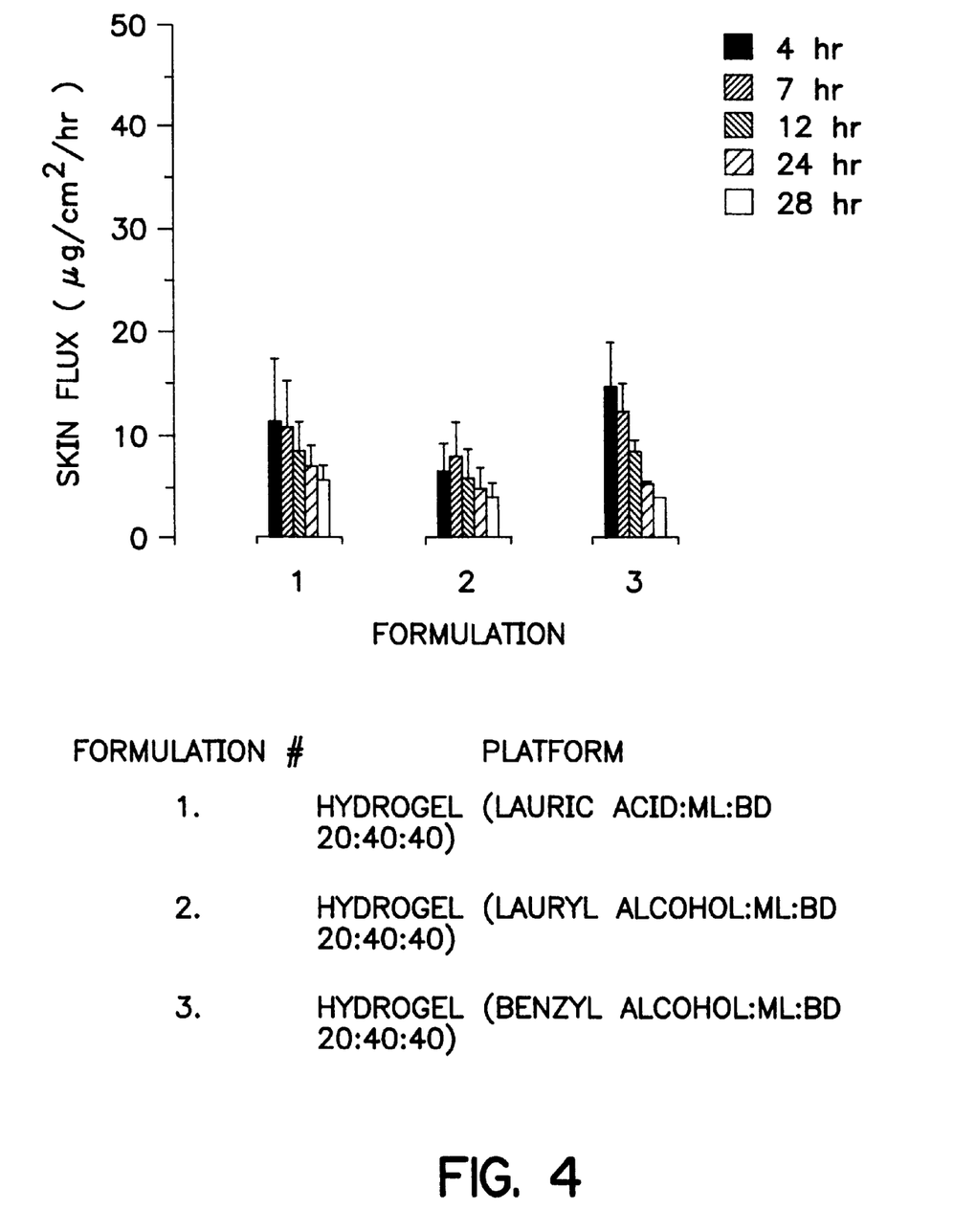
FIG. 4 represents in graph form the testosterone flux profiles from the hydrogel systems of the invention as evaluated in Example 3.
Figure 5:
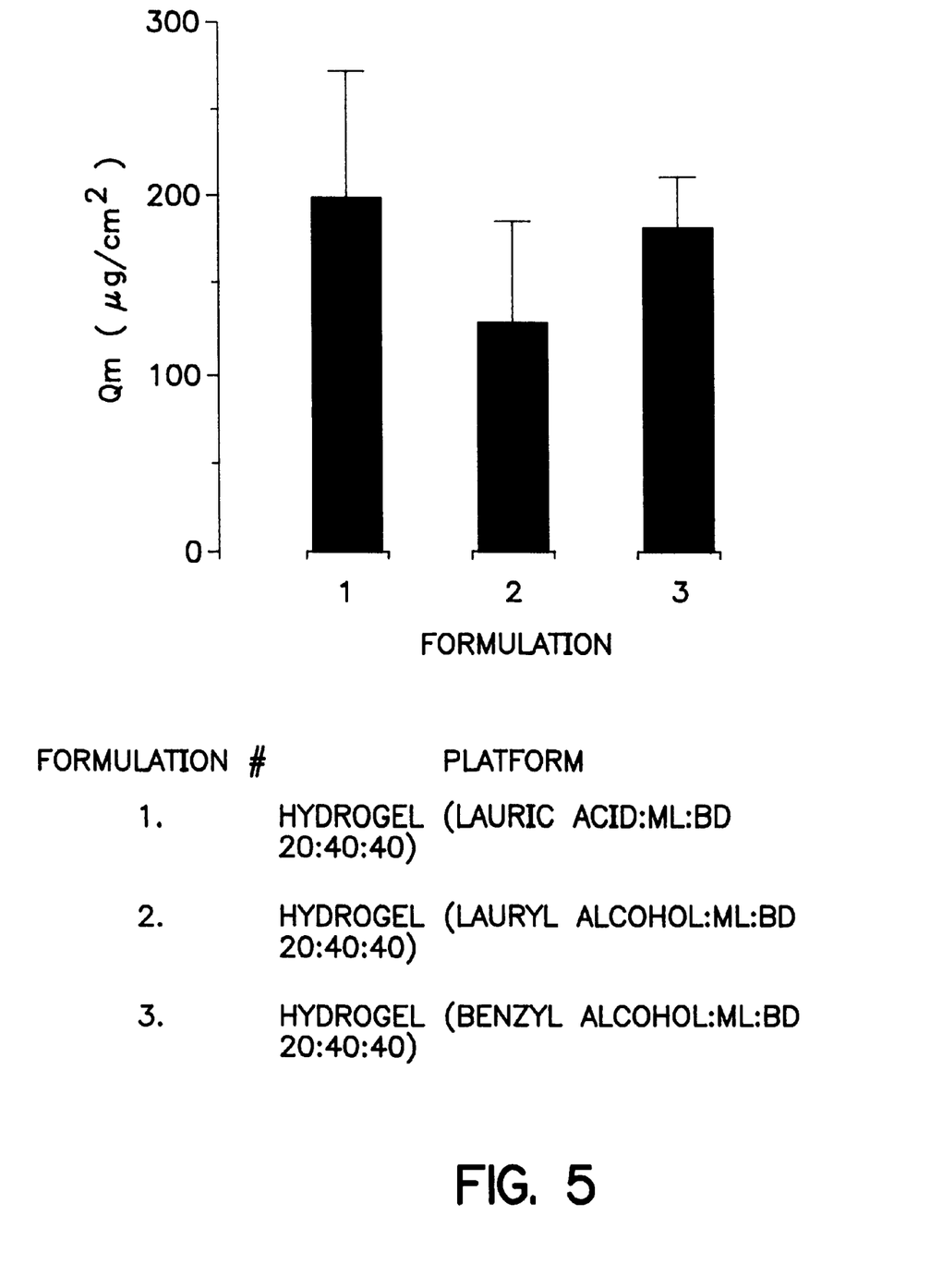
FIG. 5 represents in graph form the cumulative permeation of testosterone from hydrogel systems of the invention as evaluated in Example 3.

The formulations evaluated are listed in Table 3, along with the cumulative permeation results from various platforms. The results are also illustrated graphically in FIGS. 4 and 5.

TABLE 3

Cumulative Permeation of Tetosterone from Platforms at 24 Hours

| Formulation # | Platform | Qm (μg/cm²) |
|---|---|---|
| 1. | Hydrogel (Lauric Acid:ML:BD 20:40:40) | 198 ± 74 |
| 2. | Hydrogel (Lauryl Alcohol:ML:BD 20:40:40) | 127 ± 58 |
| 3. | Hydrogel (Benzyl Alcohol:MD:BD 20:40:40) | 181 ± 28 |

We claim:

1. A drug reservoir for use in a transdermal drug delivery system, comprising a layer of a polyurethane hydrogel having a drug formulation comprising at least one permeation enhancer absorbed therein.

2. The drug reservoir of claim 1, containing at least about 65 wt. % drug formulation.

3. The drug reservoir of claim 1, wherein the drug is a steroid drug.

4. The drug reservoir of claim 3, wherein the steroid drug is selected from the group consisting of flurogestone acetate, hydroxyprogesterone, hydroxyprogesterone acetate, hydroxyprogesterone caproate, medroxy-progesterone acetate, norethindrone, norethindrone acetate, norethisterone, norethynodrel, desogestrel, 3-keto desogestrel, gestadene, levonorgestrel, estradiol, estradiol benzoate, estradiol valerate, estradiol cyprionate, estradiol decanoate, estradiol acetate, ethynyl estradiol, estriol, estrone, mestranol, betamethasone, betamethasone acetate, cortisone, hydrocortisone, hydrocortisone acetate, corticosterone, fluocinolone acetonide, prednisolone, prednisone, triamcinolone, aldosterone, androsterone, testosterone, methyl testosterone, and combinations thereof.

5. A transdermal drug delivery system, comprising a laminated composite of: a high capacity drug reservoir of a polyurethane hydrogel having a drug formulation comprising at least one permeation enhancer contained therein; and a backing layer that is substantially impermeable to the drug and which defines the upper surface of the system during drug delivery.

6. The system of claim 5, wherein the hydrogel has sufficient tack such that it serves to maintain the system in drug transmitting relationship to the body surface.

7. The system of claim 5, further including a affixing means for ensuring that the system adheres to the body surface during drug delivery.

8. The system of claim 7, wherein the affixing means comprises a layer of a pharmaceutically acceptable, pressure-sensitive contact adhesive which serves as the basal surface of the system and adheres to the body surface during drug administration.

9. The system of claim 7, wherein the affixing means comprises a peripheral ring of a pharmaceutically acceptable, pressure-sensitive contact adhesive underlying the drug reservoir.

10. The system of claim 5, wherein the drug reservoir contains at least about 40 wt. % drug formulation.

11. The system of claim 10, wherein the drug reservoir contains at least about 65 wt. % drug formulation.

12. The system of claim 8, further including a rate-controlling membrane disposed between the drug reservoir and the contact adhesive layer.

13. The system of claim 7, wherein the drug is a steroid drug.

14. The system of claim 13, wherein the steroid drug is selected from the group consisting of flurogestone acetate, hydroxyprogesterone, hydroxyprogesterone acetate, hydroxyprogesterone caproate, medroxy-progesterone acetate, norethindrone, norethindrone acetate, norethisterone, norethynodrel, desogestrel, 3-keto desogestrel, gestadene, levonorgestrel, estradiol, estradiol benzoate, estradiol valerate, estradiol cyprionate, estradiol decanoate, estradiol acetate, ethynyl estradiol, estriol, estrone, mestranol, betamethasone, betamethasone acetate, cortisone, hydrocortisone, hydrocortisone acetate, corticosterone, fluocinolone acetonide, prednisolone, prednisone, triamcinolone, aldosterone, androsterone, testosterone, methyl testosterone, and combinations thereof.

15. The system of claim 5, wherein the permeation enhancer comprises: (a) a first component selected from the group consisting of fatty acids of the formula $CH_3(CH_2)_mCOOH$ and fatty alcohols of the formula $CH_3(CH_2)_mCH_2OH$, where m is an integer in the range of 8 to 16; (b) a second component comprising a fatty ester $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups; and (3) a third component comprising a $C_2$–$C_6$ alkanediol.

16. The system of claim 15, wherein the permeation enhancer comprises: (a) a first component selected from the group consisting of fatty acids of the formula $CH_3(CH_2)_mCOOH$ and fatty alcohols of the formula $CH_3(CH_2)_mCH_2OH$, where m is an integer in the range of 8 to 16; (b) a second component comprising a fatty ester $[CH_3(CH_2)_mCOO]_nR$ in which m is an integer in the range of 8 to 16, n is 1 or 2, and R is a lower alkyl ($C_1$–$C_3$) residue that is either unsubstituted or substituted with one or two hydroxyl groups; and (3) a third component comprising a $C_2$–$C_6$ alkanediol.

17. A method for preparing a transdermal drug delivery system having a high capacity, polyurethane hydrogel drug reservoir, comprising: (a) reacting a polyurethane with a crosslinking agent in the presence of water, for a time period effective to form a hydrogel; (b) absorbing a drug formulation comprising at least one permeation enhancer into the hydrogel to form a drug-containing hydrogel; and laminating a backing layer to the hydrogel that is substantially impermeable to the drug and serves as the upper surface of the system during drug delivery.

18. The method of claim 17, wherein steps (a) and (b) are conducted simultaneously.

19. The method of claim 17, wherein step (b) is conducted subsequent to step (a).

20. The method of claim 17, wherein step (a) results in a hydrogel of sufficient tack such that it serves to maintain the system in drug transmitting relationship to the body surface.

21. The method of claim 17, further including: step (d), providing a pharmaceutically acceptable contact adhesive as a layer immediately adjacent to the hydrogel reservoir to serve as the basal surface of the system and affix the system to the body surface during drug delivery.

22. The method of claim 17, further including: step (d), providing a pharmaceutically acceptable contact adhesive as a peripheral ring underlying the hydrogel reservoir, to affix the system to the body surface during drug delivery.

23. A method for administering a drug to a mammalian individual, comprising positioning topically on the individual a transdermal drug delivery system containing the drug reservoir of claim 1.

24. The drug reservoir of claim 1, containing at least about 40 wt. % drug formulation.

25. A drug reservoir for use in a transdermal drug delivery system, comprising a layer of a polyurethane hydrogel having a drug formulation absorbed therein, where the drug formulation comprises an androgenic agent and a permeation enhancer.

26. The drug reservoir of claim 25 wherein the androgenic agent comprises at least one androsterone, testosterone or a derivative thereof.

27. A drug reservoir for use in a transdermal drug delivery system comprising a layer of a polyurethane hydrogel having a drug formulation absorbed therein, wherein the drug formulation comprises an androgenic agent and a permeation enhancer.

* * * * *